(12) United States Patent
Heidner et al.

(10) Patent No.: US 9,486,348 B2
(45) Date of Patent: Nov. 8, 2016

(54) VASCULAR DELIVERY SYSTEM AND METHOD

(75) Inventors: Matthew C. Heidner, Maple Grove, MN (US); Bryan Patrick, Brooklyn Park, MN (US); Grant Abraham Mauch, Delano, MN (US); Mark Krans, St. Louis Park, MN (US)

(73) Assignee: S. Jude Medical, Cardiology Division, Inc., St. Paul, MN (US)

(*) Notice: Subject to any disclaimer, the term of this patent is extended or adjusted under 35 U.S.C. 154(b) by 1140 days.

(21) Appl. No.: 13/018,802

(22) Filed: Feb. 1, 2011

(65) Prior Publication Data

US 2012/0197376 A1    Aug. 2, 2012

(51) Int. Cl.
| | |
|---|---|
| A61F 2/06 | (2013.01) |
| A61F 2/966 | (2013.01) |
| A61F 2/90 | (2013.01) |
| A61F 2/95 | (2013.01) |

(52) U.S. Cl.
CPC .................. *A61F 2/966* (2013.01); *A61F 2/90* (2013.01); *A61F 2002/9517* (2013.01)

(58) Field of Classification Search
CPC .. A61F 2002/9517; A61F 2/958; A61F 2/95; A61F 2/966; A61F 2/07; A61F 2/954; A61F 2/962
USPC ............. 623/1.11, 1.12, 1.13, 1.2, 1.23, 1.34
See application file for complete search history.

(56) References Cited

U.S. PATENT DOCUMENTS

| | | | |
|---|---|---|---|
| 4,655,771 A | 4/1987 | Wallsten | |
| 4,665,918 A * | 5/1987 | Garza et al. | ................. 606/108 |
| 5,026,377 A | 6/1991 | Burton et al. | |
| 5,064,435 A | 11/1991 | Porter | |
| 5,290,295 A * | 3/1994 | Querals | ............... A61M 25/104 604/264 |
| 5,415,664 A * | 5/1995 | Pinchuk | ....................... 623/1.11 |
| 5,634,928 A * | 6/1997 | Fischell | .................... A61F 2/95 606/194 |
| 5,702,418 A | 12/1997 | Ravenscroft | |
| 5,733,267 A * | 3/1998 | Del Toro | ..................... 623/1.11 |
| 5,735,859 A * | 4/1998 | Fischell | .................... A61F 2/95 606/108 |
| 5,749,861 A * | 5/1998 | Guala et al. | .................. 604/249 |
| 5,817,102 A | 10/1998 | Johnson et al. | |
| 6,136,006 A | 10/2000 | Johnson et al. | |
| 6,190,360 B1 * | 2/2001 | Iancea et al. | ............ 604/164.09 |

(Continued)

OTHER PUBLICATIONS

International Search Report and Written Opinion for International Application No. PCT/US2012/023245, mailed Jun. 4, 2012.

*Primary Examiner* — Melanie Tyson
*Assistant Examiner* — Erin Colello
(74) *Attorney, Agent, or Firm* — Armstrong Teasdale LLP

(57) ABSTRACT

A delivery device and method for deploying a stent-graft within a body lumen of a patient are provided. According to one embodiment, the delivery device includes a tubular member lock that couples an outer tubular member of the device with an inner tubular member, such that as the outer tubular member is retracted to deploy the stent-graft, the distal-most end of the delivery device is also retracted. In one embodiment, the delivery device also includes a stent lock disposed on an intermediate tubular member that is configured to releasably couple the stent-graft and the intermediate tubular member. The inner tubular member and the outer tubular member are configured to be coupled to one another such that movement of the outer tubular member results in movement of the inner tubular member with respect to the intermediate tubular member so as to deploy the stent-graft.

26 Claims, 8 Drawing Sheets

(56) References Cited

U.S. PATENT DOCUMENTS

| | | |
|---|---|---|
| 6,287,329 B1 | 9/2001 | Duerig et al. |
| 6,299,636 B1 | 10/2001 | Schmitt et al. |
| 6,514,261 B1 | 2/2003 | Randall et al. |
| 6,517,547 B1 | 2/2003 | Feeser et al. |
| 6,623,518 B2* | 9/2003 | Thompson et al. .......... 623/1.11 |
| 6,699,274 B2 | 3/2004 | Stinson |
| 6,945,990 B2* | 9/2005 | Greenan ....................... 623/1.12 |
| 6,953,475 B2* | 10/2005 | Shaolian et al. ............. 623/1.11 |
| 6,984,244 B2* | 1/2006 | Perez ......................... A61F 2/07 604/103.05 |
| 7,052,511 B2 | 5/2006 | Weldon et al. |
| 7,127,789 B2 | 10/2006 | Stinson |
| 7,264,632 B2* | 9/2007 | Wright ....................... A61F 2/95 623/1.11 |
| 7,763,063 B2* | 7/2010 | Arbefeuille ............... A61F 2/07 623/1.11 |
| 7,947,070 B2* | 5/2011 | Headley et al. ............. 623/1.11 |
| 8,062,349 B2* | 11/2011 | Moore ....................... A61F 2/07 623/1.11 |
| 8,070,790 B2* | 12/2011 | Berra ......................... A61F 2/07 623/1.11 |
| 8,500,792 B2* | 8/2013 | Berra ......................... A61F 2/07 623/1.12 |
| 2001/0049554 A1 | 12/2001 | Ruiz et al. |
| 2002/0120322 A1* | 8/2002 | Thompson et al. .......... 623/1.11 |
| 2003/0236493 A1* | 12/2003 | Mauch ....................... 604/95.04 |
| 2004/0230284 A1* | 11/2004 | Headley et al. ............. 623/1.11 |
| 2005/0038495 A1* | 2/2005 | Greenan ................... A61F 2/95 623/1.11 |
| 2005/0049667 A1* | 3/2005 | Arbefeuille ............... A61F 2/07 623/1.11 |
| 2005/0149160 A1* | 7/2005 | McFerran ..................... 623/1.11 |
| 2006/0030817 A1* | 2/2006 | Kraus et al. ............. 604/167.01 |
| 2006/0253184 A1 | 11/2006 | Amplatz |
| 2007/0118207 A1 | 5/2007 | Amplatz et al. |
| 2007/0168019 A1 | 7/2007 | Amplatz et al. |
| 2007/0185485 A1* | 8/2007 | Hauck et al. .................. 606/41 |
| 2007/0270932 A1 | 11/2007 | Headley et al. |
| 2008/0077226 A1* | 3/2008 | Ouellette .................. A61F 2/07 623/1.11 |
| 2008/0195041 A1* | 8/2008 | Goldfarb et al. .......... 604/96.01 |
| 2009/0062841 A1 | 3/2009 | Amplatz et al. |
| 2009/0069786 A1* | 3/2009 | Vesely et al. ................. 604/500 |
| 2009/0171386 A1 | 7/2009 | Amplatz et al. |
| 2009/0192518 A1 | 7/2009 | Golden et al. |
| 2009/0210047 A1 | 8/2009 | Amplatz et al. |
| 2009/0210048 A1 | 8/2009 | Amplatz et al. |
| 2010/0023046 A1 | 1/2010 | Heidner et al. |
| 2010/0030255 A1* | 2/2010 | Berra et al. .................. 606/200 |
| 2010/0030318 A1* | 2/2010 | Berra ........................... 623/1.11 |
| 2010/0234932 A1* | 9/2010 | Arbefeuille ............... A61F 2/95 623/1.11 |
| 2011/0208288 A1* | 8/2011 | Arbefeuille ............... A61F 2/07 623/1.13 |
| 2011/0218610 A1* | 9/2011 | Headley .................... A61F 2/958 623/1.11 |
| 2011/0313503 A1* | 12/2011 | Berra ......................... A61F 2/07 623/1.11 |

\* cited by examiner

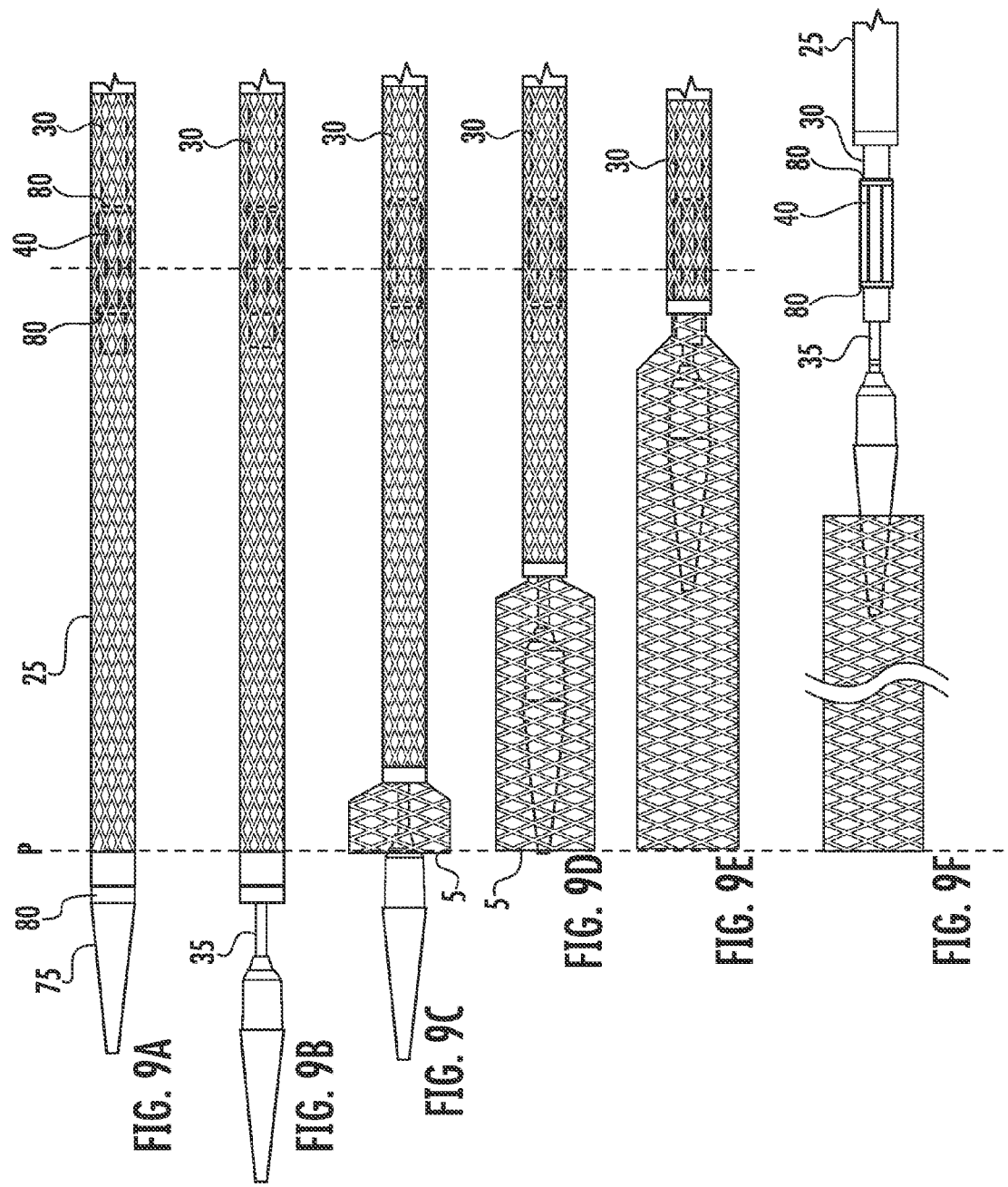

VASCULAR DELIVERY SYSTEM AND METHOD

BACKGROUND

I. Field of the Invention

Embodiments of the present invention relate generally to delivery devices and procedures for treating a localized abnormal dilation of a lumen, aneurysm, fistula, lesion or the like in certain blood vessels and internal organs. In particular, embodiments are directed to devices and methods for delivering and deploying stent-grafts in the vasculature of a patient, such as for usage in over-the-wire delivery.

II. Description of the Related Art

Various conventional braided wire stents and grafts exist to address various medical conditions in a patient's vasculature. Transluminal prostheses are well known in the medical arts for implantation in blood vessels, biliary ducts, or other similar organs of the living body. These prostheses are commonly known as stents and are used to maintain, open, or dilate tubular strictures or to support tubular structures. When bio-compatible materials are used as a covering or lining for the stent, the prosthesis is called a stent-graft or vascular graft.

Various conventional delivery systems exist for implanting or deploying braided or self-expanding stents or grafts. For example, a braided, self-expanding stent or a graft incorporating a self-expanding stent as a structural component (referred to herein as a stent-graft) may be introduced into the body by stretching the device axially, until its radial diameter is reduced sufficiently so that it can be fed into a catheter. The device is delivered through the catheter to the site of deployment and then released from the catheter whereupon the device self-expands. A simple delivery device for locating and deploying such a device may include a flexible catheter having a proximal handle and a flexible plunger having a proximal handle. The device is inserted into the distal end of the catheter and the distal end of the catheter is positioned at the site of deployment, such as an artery. The handles of the catheter may be moved relative to each other to push out or uncover the device from the distal end of the catheter.

As mentioned above, as a self-expanding stent-graft is deployed from a delivery device, the diameter of the stent-graft expands and draws the ends of the device closer to each other. In other words, the length $l_2$ of the stent-graft when it is in an expanded state (e.g., deployed from the delivery device) is shorter than the length $l_1$ of the stent-graft when it is in a contracted state (e.g., undeployed from the delivery device). An illustration of the relative lengths $l_1$, $l_2$ of a self-expanding stent-graft is shown in FIG. 1.

As a result of the shortened length $l_2$ of the expanded stent-graft (i.e., foreshortening), the placement of the stent-graft within a body lumen can be negatively affected. This is because although the distal end 15 of the stent-graft 5 (i.e., the end farthest inside the body) may be positioned in the desired location P before it is deployed from the delivery system (i.e., in the contracted state), as the stent-graft is deployed and self-expands, for example through movement of a sheath 10 in a direction A as depicted in FIG. 2 to uncover the stent-graft, the distal end 15 of the stent-graft typically moves back towards the delivery device in a direction B. To compensate for this movement and to reposition the end 15 of the stent-graft 5 in the desired location P, the user may have to move a pusher 18 of the delivery device in a direction C, as shown. As a result, a tip of the pusher 18 guiding the deployment of the stent-graft 5 may end up extending farther distally than originally anticipated and in some cases may disturb or damage the patient's vasculature.

Accordingly, there is a need for an improved delivery system that provides predictable placement of a graft in the vasculature and overcomes the shortcomings of conventional solutions.

SUMMARY OF THE INVENTION

Embodiments therefore provide a delivery device and method for deploying a stent or stent-graft within a body lumen of a patient. In general, the delivery device is configured to maintain a position of the distal end of the stent-graft such that the stent-graft may be deployed accurately without substantial advancement of a distal end of the delivery system distal to the stent-graft in the vessel, thus avoiding inadvertently contacting or damaging the patient's vasculature.

In one embodiment, a device for deploying a stent-graft within a body lumen is provided that includes an outer tubular member, an intermediate tubular member, and an inner tubular member. The outer tubular member defines an outer lumen, and the intermediate tubular member is at least partially disposed within the outer lumen and is configured to move axially therein. The intermediate tubular member defines an intermediate lumen. The inner tubular member is at least partially disposed within the intermediate lumen and is configured to move axially therein. A self-expanding stent-graft may be disposed in the outer lumen and may at least partially overlie the intermediate member. The stent-graft may be configured to move axially in cooperation with the intermediate member. The inner tubular member and the outer tubular member may be configured to be coupled to one another such that movement of the outer tubular member in an axial direction results in movement of the inner tubular member in the axial direction with respect to the intermediate tubular member so as to deploy the stent-graft. The coupling of the inner tubular and the outer tubular member also allows a single hand to control the position of the two members.

In some cases, the outer tubular member may define a first length, the intermediate tubular member may define a second length, and the inner tubular member may define a third length, where the first length is shorter than the second length and the second length is shorter than the third length. The inner tubular member may define an inner lumen configured to receive a guidewire therethrough.

The device may include a tip member attached to a distal end of the inner tubular member. A tubular member lock may also be provided that is configured to releasably couple the inner tubular member and the outer tubular member. The device may further include a stent lock disposed on the intermediate tubular member and configured to releasably couple the stent-graft and the intermediate tubular member. The stent lock may be disposed at a distal end of the intermediate tubular member. In some cases, the stent lock may be disposed within a lumen of the stent-graft, and the stent lock may be configured to couple the stent-graft and the intermediate tubular member when a portion of the stent-graft overlying the intermediate tubular member is in a contracted state within the tubular member and to uncouple the stent-graft and the intermediate tubular member when a portion of the stent-graft is in an expanded state and positioned as desired.

In some embodiments, the inner tubular member, the intermediate tubular member, and the outer tubular member are configured to move independently of each other. A first handle may be provided that is attached to a proximal end of the inner tubular member and configured to move the inner tubular member. Furthermore, a second handle may be provided that is attached to a proximal end of the outer tubular member and configured to move the outer tubular member. A third handle may be attached to a proximal end of the intermediate tubular member, and movement of one of the second handle and the third handle towards the other of the second handle and the third handle may serve to deploy the stent-graft from the outer tubular member.

In some cases, a rigid tubular member may be attached to a proximal end of the second handle and may be configured to receive at least a portion of the intermediate tubular member and the inner tubular member therethrough. The rigid tubular member may include a slot, and the third handle may be configured to engage the intermediate tubular member via the slot and to move axially along the slot. In addition, a stop may be provided that is configured to be selectively fixed to the rigid tubular member via the slot at a location between the second handle and the third handle, such that the stop serves to constrain the axial movement of the third handle along the rigid tubular member.

The stent-graft may comprise at least one layer of fabric. The layer(s) of fabric may comprise braided metal strands, and in some cases the layer(s) of fabric may comprise metallic strands and/or polymeric strands.

In other embodiments, a method for deploying a self-expanding stent-graft within a body lumen is provided. A device is initially provided that includes an outer tubular member defining an outer lumen, an intermediate tubular member, and an inner tubular member. The intermediate tubular member may be at least partially disposed within the outer lumen, and the intermediate tubular member may define an intermediate lumen. The inner tubular member may be at least partially disposed within the intermediate lumen. The device may further include a self-expanding stent-graft disposed in the outer lumen and at least partially overlying the intermediate tubular member, where the stent-graft is configured to move axially with the intermediate tubular member.

In some embodiments, the device may be positioned within a body lumen, and the inner tubular member may be locked to the outer tubular member. The outer tubular member and the inner tubular member may be retracted with respect to the intermediate tubular member, thereby deploying the stent-graft.

In some cases, a distal end of the inner tubular member may be advanced independently of the intermediate tubular member and the outer tubular member. The device may further comprise a first handle attached to a proximal end of the inner tubular member, and the step of advancing the distal end of the inner tubular member may include moving the first handle distally with respect to the outer and intermediate tubular members. Furthermore, the device may include a second handle attached to a proximal end of the outer tubular member and a third handle attached to a proximal end of the intermediate tubular member, and the step of retracting the outer tubular member and the inner tubular member may include moving the second handle towards the third handle. The movement of the third handle with respect to the second handle may in some cases be constrained. In some embodiments, the stent-graft may be recaptured fully within the outer lumen.

BRIEF DESCRIPTION OF THE DRAWINGS

The foregoing features and advantages of the invention will become apparent to those skilled in the art from the following detailed description of a preferred embodiment, especially when considered in conjunction with the accompanying drawings in which like numerals in the several views refer to corresponding parts.

FIGS. 9A-9F illustrate the deployment of a stent-graft using a delivery device according to exemplary embodiments.

DETAILED DESCRIPTION

Embodiments of the present invention now will be described more fully hereinafter with reference to the accompanying drawings, in which some, but not all embodiments of the invention are shown. Indeed, the invention may be embodied in many different forms and should not be construed as limited to the embodiments set forth herein; rather, these embodiments are provided so that this disclosure will satisfy applicable legal requirements. Like numbers refer to like elements throughout.

Figure 1:
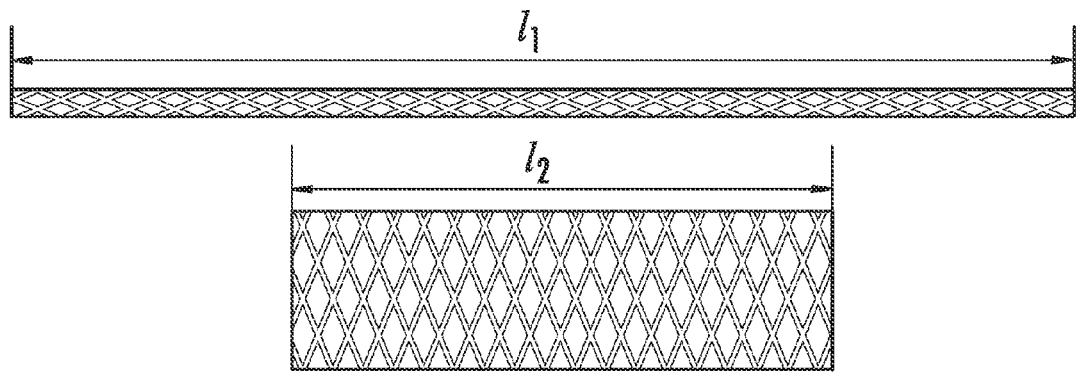
FIG. 1 is an illustration of an expandable stent-graft of the prior art in a contracted state and an expanded state.
Figure 2:
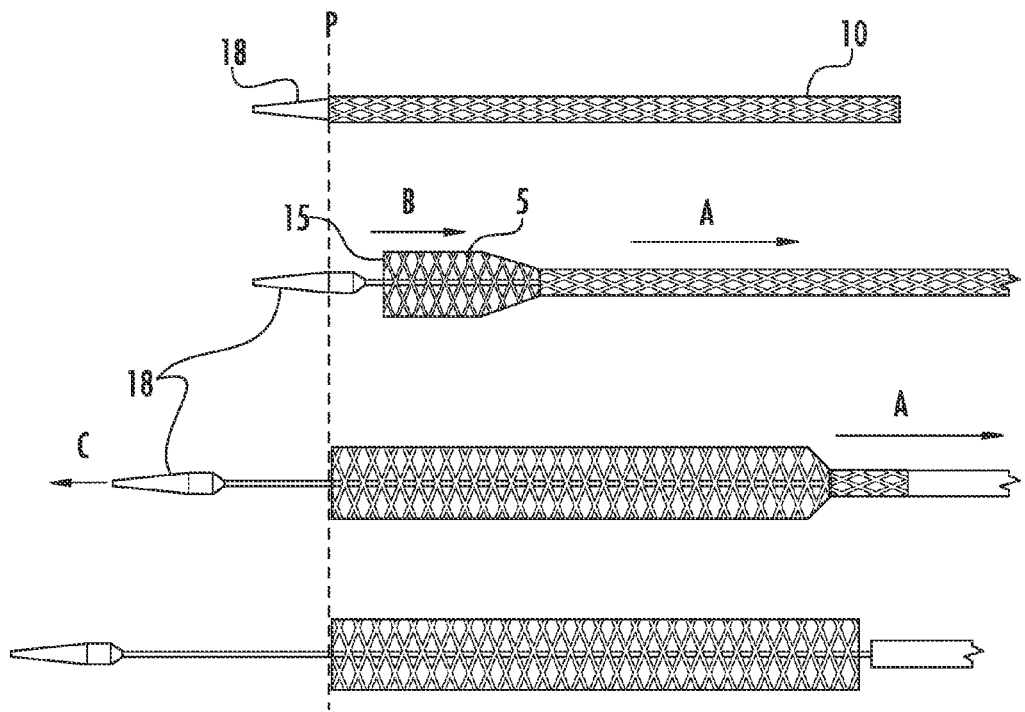
FIG. 2 is an illustration of tip advancement due to graft foreshortening in prior art devices.
Figure 3:
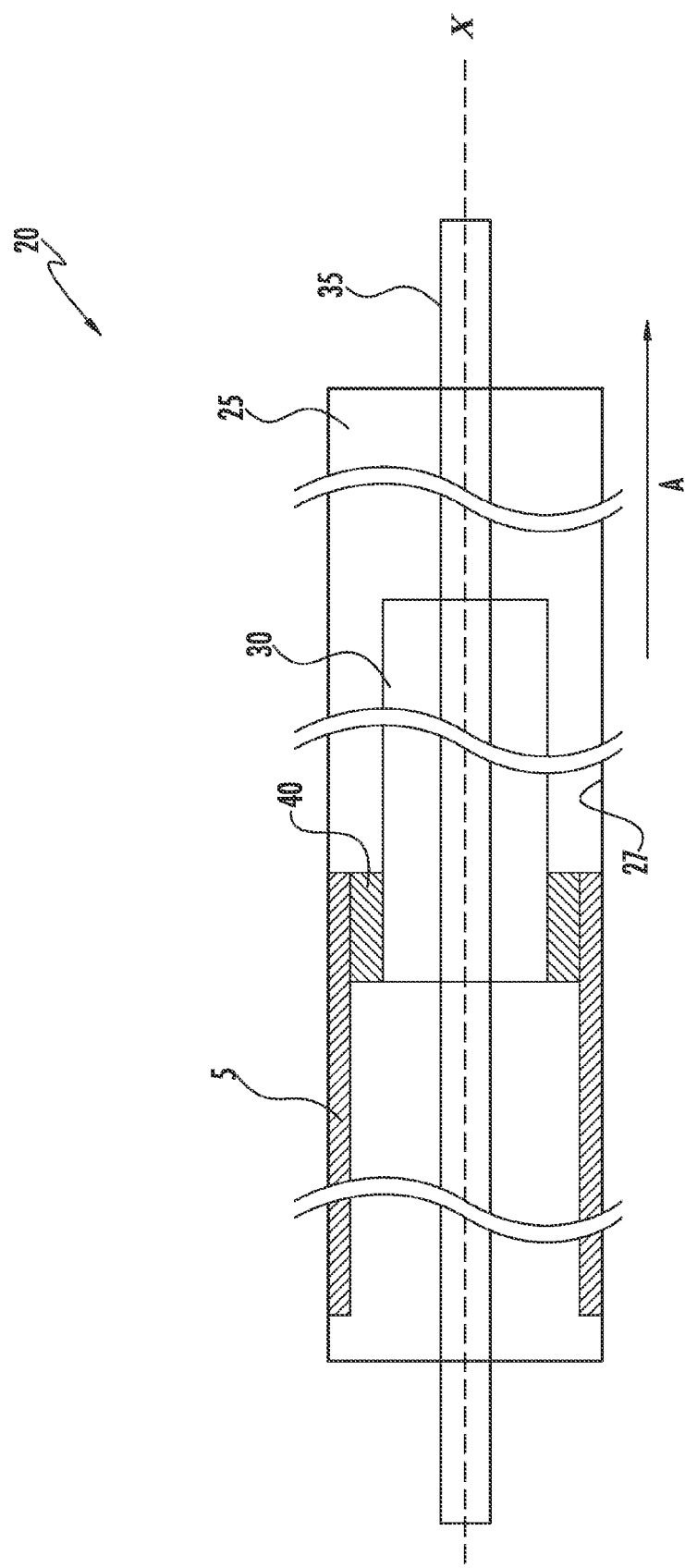
FIG. 3 is a cross-section of an outer tubular member, an intermediate tubular member, and an inner tubular member of a device according to an exemplary embodiment.

Embodiments provide a delivery device and method for deploying a stent-graft within a body lumen of a patient. In general, the delivery device is configured to maintain a position of the distal end of the stent-graft such that the stent-graft may be deployed accurately without substantial advancement of a distal end of the delivery system distal to the stent-graft in the vessel, thus avoiding inadvertently contacting or damaging the patient's vasculature A simplified cross-sectional representation of an embodiment of a delivery device 20 for deploying a self-expanding stent-graft 5 is shown in FIG. 3. The term "stent-graft" as used herein includes a self-expanding stent or a graft incorporating a self-expanding stent as a structural component. In some embodiments, the stent-graft 5 is a medical device used in treating a target site within the body, such as for excluding various vascular abnormalities, which may include, for example, excluding an aneurysm. The medical device may also be used as a stent, flow restrictor or a shunt, filter or other type of device for placement in the vascular system, as well as a graft for lining a lumen of a vessel. It is understood that the use of the term "target site" is not meant to be limiting, as the medical device may be configured to treat any target site, such as an abnormality, a vessel, an organ, an opening, a chamber, a channel, a hole, a cavity, or the like, located anywhere in the body. For example, the abnormality could be any abnormality that affects the shape or the function of the native lumen, such as an aneurysm, a lesion, a vessel dissection, flow abnormality or a tumor. Furthermore, the term "lumen" is also not meant to be limiting, as the abnormality may reside in a variety of locations within the vasculature, such as a vessel, an artery, a vein, a passageway, an organ, a cavity, or the like.

The stent-graft 5 may include one or more layers of occlusive material. In one embodiment, the layers of occlusive material are independent tubular members that are layered concentrically with respect to one another. The layers may be elongated to a reduced configuration for delivery to a target site and expand upon deployment as explained in further detail below. In another embodiment, the plurality of layers may be folded with respect to one another into a layered structure. According to one aspect, the folded layers may be configured to be separated into a non-overlapping configuration for delivery within a catheter and return to the overlapping configuration when deployed from the catheter. In the preset, overlapping configuration, the occlusive material may be configured to provide a central passageway or lumen for fluid flow therethrough (e.g., blood flow through the stent-graft).

In one embodiment, the stent-graft 5 may include a braided fabric formed of a plurality of wire strands having a predetermined relative orientation with respect to one another. Moreover, the device may comprise a plurality of layers of occlusive material such that the device may have a variety of occluding materials capable of at least partially inhibiting blood flow therethrough in order to facilitate the formation of thrombus and epithelialization around the device. Although the term "strand" is discussed herein, "strand" is not meant to be limiting, as it is understood the fabric may comprise one or more wires, cords, fibers, yarns, filaments, cables, threads, or the like, such that such terms may be used interchangeably.

As used herein, "substantially preclude or impede flow" shall mean, functionally, that blood flow may occur for a short time, e.g., about 3-60 minutes through the occlusive material, but that the body's clotting mechanism or protein or other body deposits on the braided wire strands results in occlusion or flow stoppage after this initial time period. For instance, occlusion may be clinically represented by injecting a contrast media into the upstream lumen of the device and, if no contrast media flows through the wall of the device after a predetermined period of time as viewed by fluoroscopy, the position and occlusion of the device is adequate. Moreover, occlusion of the target site could be assessed using various ultrasound echo doppler modalities.

As used herein the term "proximal" shall mean closest to the operator (less into the body) and "distal" shall mean furthest from the operator (further into the body).

According to one embodiment, the occlusive material of the stent-graft 5 is a metal fabric including a plurality of strands, such as two sets of essentially parallel generally helical strands, with the strands of one set having a "hand," i.e., a direction of rotation, opposite that of the other set. The strands may be braided, interwoven, or otherwise combined to define a generally tubular fabric. The pitch of the strands (i.e., the angle defined between the turns of the strands and the axis of the braid) and the pick of the fabric (i.e., the number of wire strand crossovers per unit length) may be adjusted as desired for a particular application. The wire strands of the metal fabric used in one embodiment of the present method may be formed of a material that is both resilient and can be heat treated to substantially set a desired shape. One factor in choosing a suitable material for the wire strands is that the wires retain a suitable amount of the deformation induced by the molding surface (as described below) when subjected to a predetermined heat treatment and elastically return to said molded shape after substantial deformation.

One class of materials that meets these qualifications is so-called shape memory alloys. One particularly preferred shape memory alloy for use in the present method is Nickel Titanium (NiTi) alloy, also known as Nitinol. Nitinol alloys are also very elastic and are said to be "superelastic" or "pseudoelastic." This elasticity may allow the device to return to a preset expanded configuration for deployment following passage in a distorted form through a delivery catheter. It is also understood that the device may comprise various materials other than Nitinol that have elastic properties, such as spring stainless steel and trade named alloys such as Elgiloy®, Hastelloy®, Phynox®, MP35N, or CoCrMo alloys. Polymeric materials may also be employed. Depending on the individual material selected, the wire strand diameter, the number of wire strands, and the pitch may be altered to achieve the desired properties of the device. Moreover, other suitable materials include those that are compatible with magnetic resonance imaging (MRI), as some materials may cause heat or torque resulting from performing MRI, and some materials may distort the MRI image. Thus, metallic and/or non-metallic materials that reduce or eliminate the potential problems resulting from the use of MRI may be employed.

A stent-graft 5 may be formed by cutting an appropriately sized piece of the fabric from a larger piece of fabric that is formed, for example, by braiding wire strands to form a long tubular braid. When cutting the fabric to the desired dimensions, one may solder, braze, weld, coat, glue, clamp, tie or otherwise affix the ends of the desired length together to minimize the risk of unraveling. According to one embodiment, each layer of the device may comprise 36-144 wire strands ranging in diameter from about 0.001 to 0.006 in. formed of a shape memory alloy, such as Nitinol, that are braided so as to define fenestrations with an area of about 0.0001 to 0.015 sq. in. Inner and outer braided layers may have pitch angles that are about equal to obtain desirable collapse and expansion characteristics, such as maintaining a uniform overall length.

Once an appropriately sized piece of the metal fabric is obtained, the fabric is deformed to generally conform to a surface of a molding element. Deforming the fabric will reorient the relative positions of the wire strands of the metal fabric from their initial order to a second, reoriented configuration. The shape of the molding element may be selected to deform the fabric into substantially the shape of the desired medical device when unconstrained. Once the molding element is assembled with the metal fabric generally conforming to a molding surface of that element, the fabric may be subjected to a heat treatment while it remains in contact with that molding surface. After the heat treatment, the fabric is removed from contact with the molding element and will substantially retain its shape in a deformed state. Different configurations of devices may be formed and heat set for various locations within the body.

Those skilled in the art will appreciate that in order to speed up the occlusion of the vessel, the device may be coated with a suitable thrombogenic agent, filled with a polyester fiber, or braided with an increased number of wire strands. The interwoven fiber may attach to a clot to retain the clot firmly within the device as it forms the occlusion.

The stent-graft 5 may include a plurality of planes of occlusion. A plane of occlusion may be any surface, whether flat or irregular in shape, that may be oriented at least partially transverse to the flow of blood so as to facilitate the formation of thrombus. At least one plane of occlusion may include one or more layers of occlusive material, such as a layer of fabric and/or a layer of polyester fiber, two layers of metal, or two layers of polyester. Thus, by modifying the configuration of the device, the number of planes of occlusion may be modified, and by changing the number of layers of occlusive material, the rate at which the device occludes the vascular abnormality may also be modified.

A stent-graft having a preselected shape may be used to treat a physiological condition of a patient. A catheter or other suitable delivery device may be positioned within a channel in a patient's body to place the distal end of the delivery device adjacent the desired treatment site, such as immediately adjacent an aneurysm, so as to bridge or exclude the aneurysm with the stent-graft.

In one embodiment, the stent-graft 5, the delivery device 20, and the delivery catheter/sheath (not shown) accommodate a coaxial guidewire that slideably passes through the stent-graft, delivery device, and delivery catheter/sheath central lumen, and therefore aids in guiding the delivery device and delivery catheter/sheath to the desired location as well as maintains the wire position across the target site in case a catheter exchange is needed. The guidewire may be delivered independently through the vasculature and across the targeted treatment location or may be extended partially distal to the distal end of the delivery device and catheter/sheath so that the wire and catheter may be advanced together. In another embodiment, the catheter/sheath is steerable to assist in placement of the stent-graft 5. For further discussion regarding a stent-graft 5 that may be inserted using the delivery device 20 and methods discussed herein, see U.S. patent application Ser. No. 11/654,288, filed on Jan. 17, 2007; Ser. No. 12/032,938, filed on Feb. 18, 2008; Ser. No. 12/032,944, filed on Feb. 18, 2008; and Ser. No. 12/179,157, filed on Jul. 24, 2008, each of which is hereby incorporated in its entirety by reference.

Referring again to FIG. 3, the delivery device 20 includes an outer tubular member 25, an intermediate tubular member 30, and an inner tubular member 35. The outer tubular member 25 defines an outer lumen, and the intermediate tubular member 30 is at least partially disposed within the outer lumen. In turn, the intermediate tubular member 30 defines an intermediate lumen, and the inner tubular member 35 is at least partially disposed within the intermediate lumen. In some embodiments, such as over-the-wire (OTW) embodiments, the inner tubular member 35 may define an inner lumen that is configured to receive a guidewire therethrough.

The stent-graft 5 may be disposed in the outer lumen and may at least partially overlie the intermediate tubular member 30. In this regard, the outer tubular member 25 may define a first length, the intermediate tubular member 30 may define a second length, and the inner tubular member 35 may define a third length. According to one embodiment, the first length may be shorter than the second length, and the second length may be shorter than the third length. The outer tubular member 25, the intermediate tubular member 30, and the inner tubular member 35 may be axially movable relative to one another along a longitudinal axis.

The stent-graft 5 may releasably be engaged with the intermediate tubular member 30 such that movement of the intermediate tubular member along an axis X of the device 20 may in turn move the stent-graft 5 out of or into the outer tubular member 25, or, alternatively, movement of the outer tubular member relative to the intermediate tubular member would not result in movement of the proximal end of the stent-graft relative to the intermediate tubular member. According to one embodiment, the outer tubular member 25 may be made of a braided PEBAX tubing, and an inner surface of the outer tubular member may be lined with PTFE to provide low friction for movement of the intermediate tubular member 30 within the outer lumen and to provide low friction for movement between the outer tubular member 25 and the stent-graft 5. The outer tubular member 25 may include a radiopaque marker band such as a platinum-iridium alloy at the distal end to allow angiographic visualization of the sheath position relative to the stent-graft. The intermediate tubular member 30 and the inner tubular member 35 may comprise polyimide tubing and may, in some cases, also include a low-friction PTFE lining.

A stent lock 40 may be provided to engage the stent-graft 5 with the intermediate tubular member 30. The stent-lock 40 may be disposed at a distal end of the intermediate tubular member 30 and may be configured to grip a proximal end of the stent-graft 5. For example, the stent lock 40 may be cylindrical and may define an inside diameter that is designed to be coupled to the intermediate tubular member 30 via a friction fit. The stent lock 40 may be made of a polymeric material such as an elastomeric material (e.g., silicone) and, in some cases, may be bonded to the intermediate tubular member 30 using adhesives or thermal bonding or coupled to the intermediate tubular member via another suitable attachment technique, such as overmolding or roll coating a polymer and solvent dispersion.

Thus, although the stent-graft 5 may be configured to slide along an inner surface 27 of the outer tubular member 25, the stent-graft proximal end may be held in position relative to the distal end of the intermediate tubular member 30 such that axial movement of the outer tubular member 25 does not result in the axial movement of the proximal end of the stent-graft relative to the intermediate tubular member 30 as long as the diameter of the stent-graft is constrained by the outer tubular member 25 in the region of the stent lock 40. In other words, the high friction between the outer surface of the stent lock 40 and the inner surface of the stent-graft 5 is greater than the friction between the inner surface 27 of the outer tubular member 25 and the outer surface of the stent-graft. Thus, the stent lock 40 may be configured to couple the stent-graft 5 and the intermediate tubular member 30 when a portion of the stent-graft overlying the intermediate tubular member is in a contracted state. As a result, as the outer tubular member 25 is moved in the direction A with respect to the intermediate tubular member 30, the proximal end of the stent-graft 5 is held fixed to the intermediate tubular member by the stent lock 40, thereby allowing the outer tubular member to slide over the stent-graft and allowing the stent-graft to self-expand when unconstrained by the outer tubular member.

As the stent-graft 5 is released and proceeds to self-expand, self-expansion in the region of the stent lock 40 (i.e., as the outer tubular member 25 is slid over and off the stent lock) in turn releases the grip between the stent-graft and the stent lock, and the stent-graft is no longer coupled to the intermediate tubular member. In other words, the stent-graft 5 and the intermediate tubular member 30 may be uncoupled when the portion of the stent-graft overlying the intermediate tubular member is allowed to self-expand by removal of the restraining force of the outer tubular member 25 over the stent lock 40. Although the stent lock 40 is shown coupled to or engaged with the stent-graft 5 at a proximal end of the stent-graft in FIG. 3, the stent lock may engage the stent-graft distally of the proximal end, such as at a middle portion of the stent-graft. An example is shown in FIGS. 9A-9F.

According to embodiments of the invention, the inner tubular member 35 and the outer tubular member 25 may be configured such that movement of the outer tubular member in an axial direction (e.g., in the direction A) results in movement of the inner tubular member in the axial direction. For example, with reference to FIG. 4, a tubular member lock 50 may be provided that is configured to releasably affix the inner tubular member 35 to the outer tubular member 25.

Figure 5:
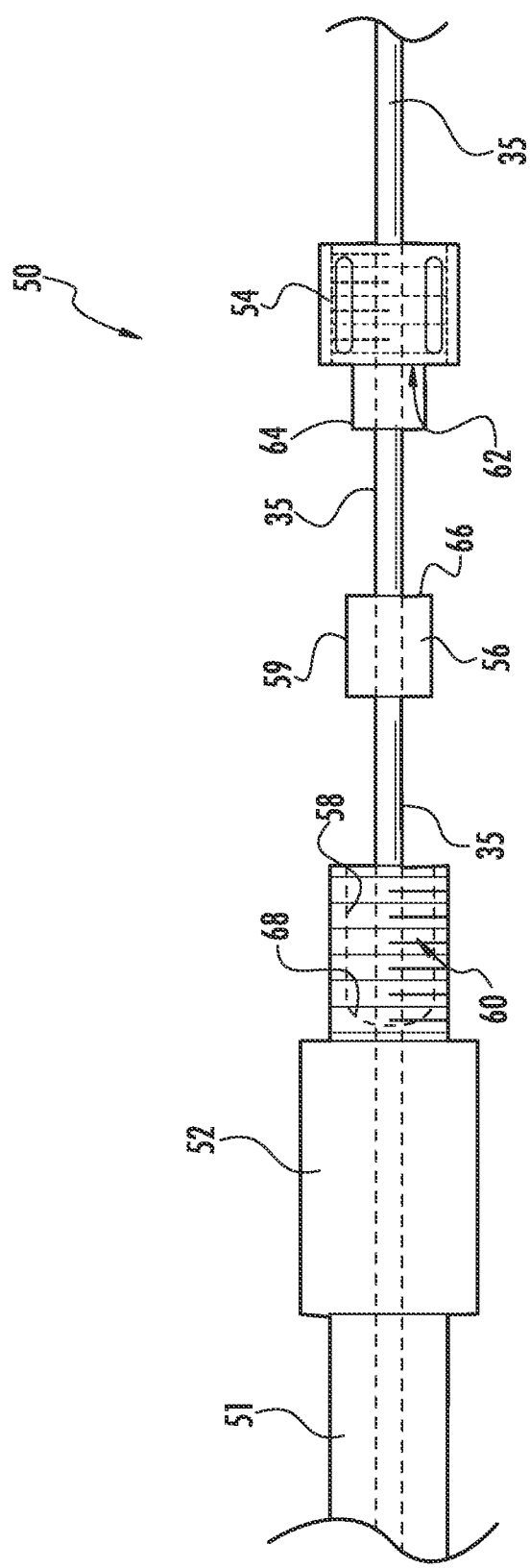
FIG. 5 is a close-up cross-sectional view of the tubular member lock of FIG. 4 in a disassembled configuration.

The tubular member lock 50 may be configured, for example, as shown in FIG. 5. With reference to FIG. 5, the tubular member lock 50 may include a lock housing 52, a pressing member 54, and a resilient sleeve 56. The lock housing 52 may be fixed to the outer tubular member (directly or through connection with a rigid connecting member 51, as shown) and may define a cavity 58 at a proximal end configured to receive the resilient sleeve 56 therein. The proximal end of the lock housing 52 may further define external threads 60 that are configured to engage internal threads 62 of the pressing member 54. Furthermore, the pressing member 54 may have a pressing surface 64 that is configured to engage a corresponding surface 66 of the resilient sleeve 56. The lock housing 52, resilient sleeve 56, and pressing member 54 may comprise a Tuohy Borst Adapter. Each of the lock housing 52, the pressing member 54, and the resilient sleeve 56 may define a lumen through which the inner tubular member 35 is received.

Figure 4:
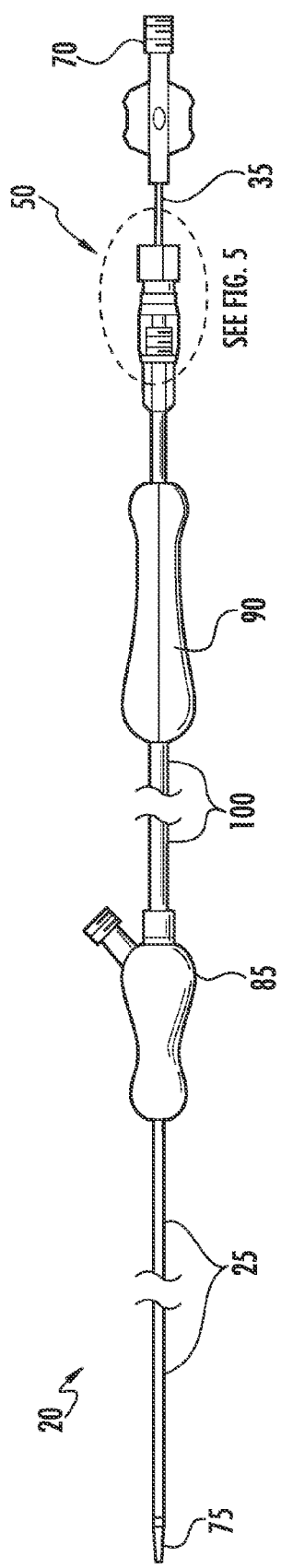
FIG. 4 is a schematic illustration of a device according to an exemplary embodiment showing a first handle, a second handle, a third handle, and a tubular member lock.

The tubular member lock 50 may be used to couple the inner tubular member 35 with the outer tubular member 25 by sliding the pressing member 54 along the inner tubular member towards the lock housing 52 and engaging the internal threads 62 of the pressing member 54 with the external threads 60 of the lock housing 52. As the pressing member 54 is moved towards the lock housing 52, the pressing surface 64 of the pressing member 54 may contact the corresponding surface 66 of the resilient sleeve 56 and move the resilient sleeve 56 into the cavity 58 of the lock housing 52 such that an outer surface 59 of the resilient sleeve 56 contacts an inner surface 68 of the cavity 58 of the lock housing 52. Because the lock housing 52 is fixed to the outer tubular member 25, thus engaged (as shown in FIG. 4), the inner tubular member 35 and the outer tubular member may be moved together as a unit. When the inner tubular member 35 and the outer tubular member 25 are not engaged, however, they are able to move independently of each other and independently of the intermediate tubular member 30, as described in greater detail below.

Turning again to FIG. 4, the device 20 may include a first handle 70 attached to a proximal end of the inner tubular member 35 that is configured to move the inner tubular member. The first handle 70 may be configured with a lumen that is aligned with the lumen of the inner tubular member 35, such as for passing a guidewire therethrough. For example, the first handle 70 may be press fit, bonded, or otherwise affixed to the proximal end of the inner tubular member 35 such that, when the inner tubular member is not coupled to the outer tubular member 25, the first handle can be pulled or pushed axially to advance or retract a distal end of the inner tubular member.

In some cases, a tip member 75 is attached to the distal end of the inner tubular member 35, as shown in FIGS. 9A-9F. Thus, a user may manipulate the first handle 70 to achieve a desired position of the tip member 75 with respect to the outer tubular member 25, for example. The tip member 75 may be fixed to the inner tubular member 35 to facilitate the insertion of the device 20 into a body lumen, for example by minimizing trauma to the vascular tissue that may be caused by the distal end of the inner tubular member during positioning of the device. In addition, the configuration of the tip member 75 may allow for more precise positioning and placement of the device 20.

In this regard, the tip member 75 may be made of a flexible polymeric material, such as silicone, and may be tapered, as shown in FIGS. 9A-9F, to minimize the risk of vessel damage and agitation. More specifically, in some embodiments, the tip member 75 may define a maximum diameter near a proximal end of the tip member that is approximately the same diameter as that of the outer tubular member 25, such that the tip member cannot be received completely within the outer lumen but, rather, forms an extension of the outer tubular member when positioned such that it abuts the distal end of the outer tubular member. The diameter of the tip member 75 may be tapered, so that the diameter defined at the distal end of the tip member is smaller than the diameter near the proximal end and in some cases approximates the outer diameter of the inner tubular member 35.

The proximal end of the tip member 75 may extend into the outer tubular member 25, as shown in FIGS. 9A-9F, and may have a proximal outer diameter and length portion configured to align with and pilot into the distal end of the outer lumen of the outer tubular member 25 to help support the tip. The tip member 75 may have a lumen that aligns with and continues the inner lumen of the inner tubular member 35.

As the tip member 75 may be made of a material such as silicone that is invisible to fluoroscopy, marker bands 80 made of a radiopaque material such as a platinum-iridium alloy may be attached to the tip member 75 as well as on either end of the silicone stent lock 40 (as shown in FIGS. 9A-9F) to assist in the proper placement of the device 20. Alternatively, radiopaque materials such as tungsten or barium sulphate may be formulated with the polymer tip 75 and/or stent lock 40 to provide fluoroscopic visibility.

Figure 8:
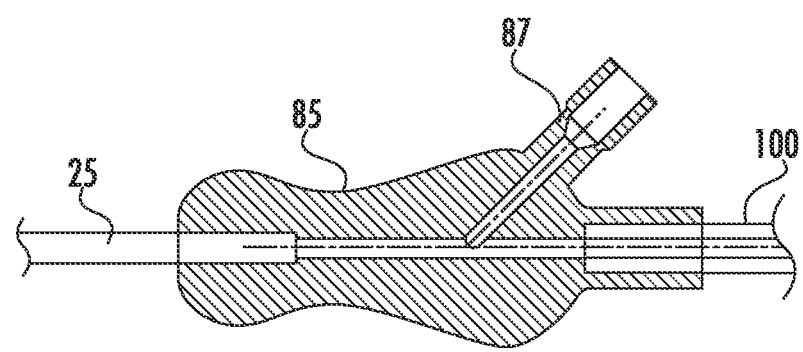
FIG. 8 is a cross-sectional view of the second handle of FIG. 6.

Turning again to FIG. 4, a second handle 85 may be provided that is configured to move the outer tubular member 25 to deploy the stent-graft, as described below. The second handle 85, shown in FIGS. 6 and 8, may be attached to a proximal end of the outer tubular member 25. In some cases, the second handle 85 may include a central lumen and a fluid port 87 that allows fluid, such as saline solution, to be introduced into the outer lumen of the outer tubular member 25 for flushing the outer lumen or otherwise delivering the fluid through the outer tubular member.

Figure 6:
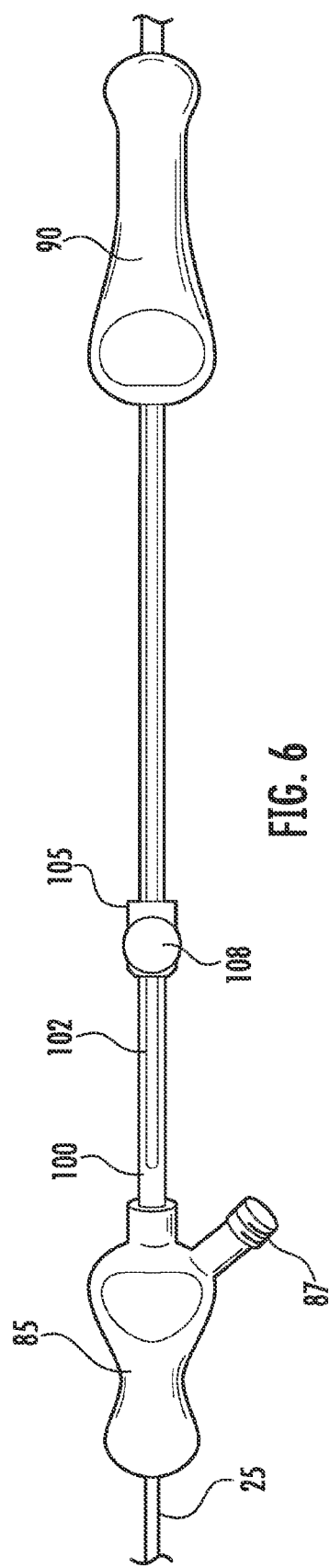
FIG. 6 is an illustration of a second handle and a third handle according to an exemplary embodiment.
Figure 7:
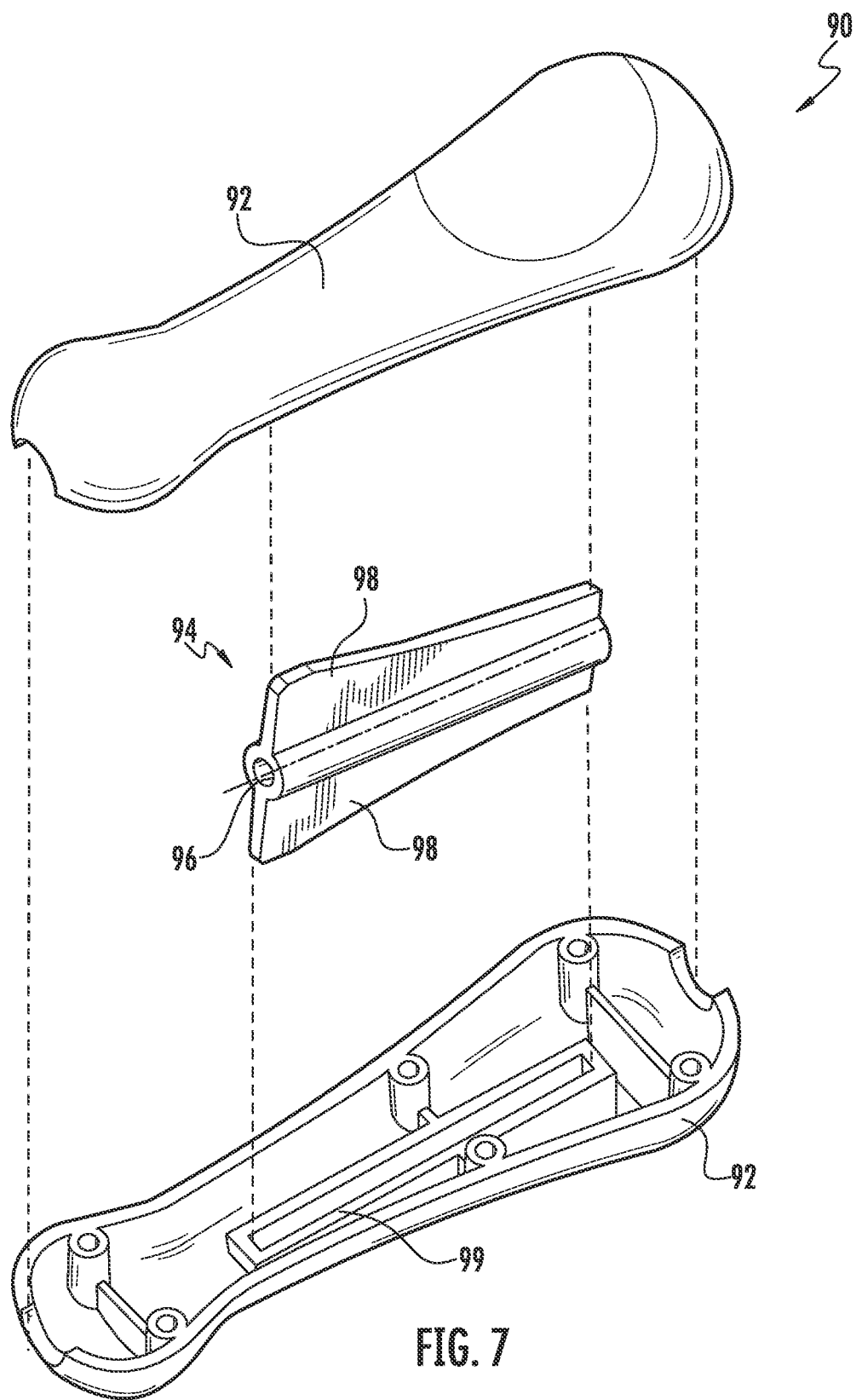
FIG. 7 is an exploded view of the third handle of FIG. 6

Referring to FIGS. 4 and 6, the device 20 may further include a third handle 90 attached to a proximal end of the intermediate tubular member 30 such that movement of one of the second handle 85 and third handle 90 towards the other of the two handles serves to deploy the stent-graft from the outer tubular member 25. The third handle 90 may comprise first and second housings 92 configured to receive an adapter 94 therebetween, as shown in FIG. 7. The adapter 94 may define an elongated cavity 96 that is configured to surround and/or otherwise engage a portion of the intermediate tubular member. The adapter 94 may also define fins 98 that are configured to be received in corresponding slots 99 of the first and second housings 92, thereby fixing the third handle 90 to the intermediate tubular member 30.

The proximal end of the second handle 85 may be attached to a rigid tubular member 100, and the third handle 90 may be configured to engage the intermediate tubular member 30 via a slot 102 in the rigid tubular member, as shown in FIG. 6. For example, the rigid tubular member 100 may in some cases be a slotted metal hypo tube. At least a portion of the intermediate tubular member 30 and the inner tubular member 35 may be received within the rigid tubular member 100 and elongated cavity 96 of the adapter 94. The third handle 90 may be used to axially position the intermediate tubular member 30. Thus, in the example shown in FIG. 7, two opposing slots 102 would be provided in the rigid tubular member 100, and each fin 98 would extend from the adapter 94, through the respective slots, and attach to the first and second housings 92. As illustrated in FIG. 6, the third handle 90 is configured to move axially along the slot 102. Therefore, a user may move the outer tubular member 25 with respect to the intermediate tubular member 30 by holding the second handle 85 (which is coupled to the outer tubular housing) and the third handle 90 (which is coupled to the intermediate tubular member) and moving the two handles with respect to each other.

In some embodiments, a stop 105 may be provided that is configured to be selectively fixed to the rigid tubular member 100 via the slot 102 at a location between the second handle 85 and the third handle 90. The stop 105 may, for example, include a screw 108 that can be tightened to fix the stop to the rigid tubular member 100 or loosened to allow the stop to move axially along the slot 102. In this way, the stop 105 may serve to constrain the axial movement of the second handle 85 relative to the third handle 90 along the rigid tubular member 100 and may thus act as a safety mechanism in the deployment procedure to prevent unintended release of the stent-graft 5, as described in greater detail below.

Using a delivery device 20 such as one described above, a medical practitioner can deploy a stent-graft within a body lumen. With reference to FIG. 4 and FIG. 9A, the device 20 is first introduced into the body lumen in a closed configuration (i.e., non-deployed configuration), in which, for example, the stent-graft 5 is fully contained within the outer tubular member 25. In over-the wire (OTW) embodiments, a coaxial guidewire may be slideably passed through the stent-graft 5 and the delivery device 20 to help guide the delivery device to the desired location.

In embodiments in which the device 20 includes a tapered tip member 75, the tip member may extend distally out from the distal end of the outer tubular member 25, thereby providing a tapered end to facilitate guidance of the device through the body lumen and minimize trauma to the vascular tissue, as noted above. In some cases, the medical practitioner may use fluoroscopy techniques to detect radiopaque marker bands 80 included on the distal end of the outer tubular member 25 and on the stent lock 40 to allow for more accurate positioning of the device 20 within the body lumen. The entire stent-graft 5, in some cases, may be visible using fluoroscopy, such as when dense Nitinol braided mesh, which is sufficiently radiopaque, is used.

At this point, as shown in FIG. 9A, the catheter is positioned such that the distal end of the stent-graft 5 is located at the target site, indicated by the vertical dashed line P. In this position, the distal end of the outer tubular member 25 and the majority of the tip member 75 are positioned distal to the target line P. The tubular member lock 50 is not engaged, and each of the outer tubular member 25, the intermediate tubular member 30, and the inner tubular member 35 is independently movable with respect to the others.

In some cases, the first handle 70 may be moved towards the second handle 85 (which is held stationary) to move the tip member 75 (or the distal end of the inner tubular member 35 in cases without a tip member) distally out from the outer tubular member 25, as shown in FIG. 9B, so as to provide sufficient space for the expansion of the stent-graft 5 and to reduce friction as the outer tubular member is later retracted over the stent-graft. The advanced position of the tip member 75 is determined by advancing the first handle 70 until it contacts the pressing member 54, which acts as a stop.

Once the device 20 is in position within the body lumen with the tip member 75 advanced, the tubular member lock 50 may be engaged by rotating the pressing member 54 clockwise so as to lock the inner tubular member 35 to the outer tubular member 25. By holding the second and third handles 85, 90 and moving the second handle towards the third handle while advancing distally the third handle, the outer tubular member 25 may be retracted proximally relative to the stent-graft 5, thereby beginning to deploy the distal end of the stent-graft, as shown in FIGS. 9C-9E. Because the inner tubular member 35 is locked to the outer tubular member 25, the distal-most end of the inner tubular member (e.g., the tip member 75) is retracted through the expanded lumen of the stent-graft 5 as the outer tubular member is moved proximally.

Advancing the intermediate tubular member 30 by moving the third handle 90 in a distal direction while retracting the outer tubular member 25 by moving the second handle 85 toward the third handle moves the proximal end of the stent-graft 5 distally to compensate for stent-graft foreshortening during expansion. The amount of advancement necessary can be assessed by the medical practitioner by watching the shape of the expanding stent-graft 5 fluoroscopically. If the stent-graft 5 has a long taper between the distal expanded end and the end of the outer tubular member 25, as seen by observing the radiopaque marker 80 at the end of the outer tubular member, for example, then the medical practitioner may need to increase the advancement of the intermediate tubular member 30 to allow the stent-graft 5 to fully self-expand against the arterial wall. In other words, the intermediate tubular member 30 should be advanced distally as the outer tubular member 25 is retracted proximally such that the stent-graft 5 expands against the vessel wall near the distal end of the outer tubular member.

In some cases, as depicted in FIG. 9C, the medical practitioner may begin to retract the outer tubular member 25 prior to locking the inner and outer tubular members 35, 25 so as to create some distance between the proximal end of the tip member 75 and the distal end of the outer tubular member. Once enough distance has been created, e.g., to allow the tip member 75 to easily pass through the expanded diameter of the stent-graft 5 without impeding the deployment of the stent-graft, the tubular member lock 50 may be engaged, and the tip member may be retracted at the same time that the outer tubular member is continuing to be retracted to deploy the stent-graft, as shown in FIGS. 9D and 9E. In a similar fashion, during retraction of the outer tubular member 25 via movement of the second handle 85 to deploy the stent-graft 5, the intermediate tubular member 30 may be advanced distally via movement of the third handle 90 to compensate for stent-graft foreshortening. In this way, the medical practitioner can maintain the position of the distal end of the stent-graft 5 during deployment, thereby reducing the need to reposition the delivery device 20 farther into the body lumen to compensate for foreshortening. There is also a reduced risk of damage to the distal vascular tissue because the distal tip does not advance distally through the vessel during deployment of the stent-graft, unlike prior art delivery devices.

In FIG. 9E, the outer tubular member 25 is shown proximally retracted as far as possible, as the movement is limited by the contact between the prepositioned stop 105 and the third handle 90 (shown in FIG. 6). The maximum retraction position of the outer tubular member 25 represents the point at which further retraction of the outer tubular member may cause release of the stent-graft 5 or a limitation in the ability to reverse the deployment process and retrieve the stent-graft back into the outer tubular member. As long as the stop 105 has not been moved, the medical practitioner may be able to recapture the stent-graft within the outer lumen of the outer tubular member in some cases, such as if the device needs to be repositioned. As noted above with respect to FIG. 3, recapture of the stent-graft 5 may be possible by moving the second handle 85 away from the third handle 90 (shown in FIG. 4), as the stent lock 40 is still in engagement with the stent-graft. During this process, the medical practitioner may move the third handle 90 proximally to compensate for the added length of a retracted stent-graft 5 (i.e., the length added due to elongation of the stent-graft as it is collapsed and retracted into the outer tubular member 25).

If the medical practitioner is satisfied that the stent-graft 5 is adequately positioned in the vessel and wishes to release the stent-graft from the delivery device 20, the screw 108 of the stop 105 may be loosened to allow the stop to slide distally toward the second handle 85 and no longer limit the retraction of the outer tubular member 25. By moving the second handle 85 toward the third handle 90 while advancing the third handle distally, the distal marker band 80 on the outer tubular member 25 may be seen fluoroscopically to move proximally over the stent lock 40 marker bands, at which point the proximal end of the stent-graft 5 is released to fully self-expand against the vessel wall. This position of a released stent-graft is depicted in FIG. 9F.

In some embodiments, the delivery device 20 may be configured such that one or more of the steps depicted in FIGS. 9A-9F and described above are done automatically, i.e., without intervention by the user of the device. For example, embodiments are contemplated in which a delivery device has a single handle or housing that incorporates a mechanism such as a gear/rack assembly for automatically moving the tip member 75 distally with respect to the outer tubular member 25 (FIG. 9C) and subsequently locking the outer tubular member to the inner tubular member 35 as the stent-graft 5 is deployed (FIGS. 9D-9F) while also automatically advancing the intermediate tubular member 30 a sufficient distance distally to compensate for stent-graft foreshortening. Such a system allows the physician to position the delivery device 20 at the target site and then maintain the handle/housing in a stationary position while performing the deployment.

This invention has been described herein in considerable detail in order to comply with the Patent Statutes and to provide those skilled in the art with the information needed to apply the novel principles and to construct and use embodiments of the example as required. However, it is to be understood that specifically different devices can carry out the invention and that various modifications can be accomplished without departing from the scope of the invention itself. For example, options shown for one embodiment could easily be applied to other embodiments, as desired for a particular application, without departing from the scope of this invention.

That which is claimed:

1. A device for deploying a stent-graft within a body lumen comprising:
   an outer tubular member defining an outer lumen;
   an intermediate tubular member at least partially disposed within the outer lumen and configured to move axially therein, wherein the intermediate tubular member defines an intermediate lumen;
   an inner tubular member at least partially disposed within the intermediate lumen and configured to move axially therein;
   a self-expanding stent-graft disposed in the outer lumen and at least partially overlying the intermediate member, wherein the stent-graft is configured to move axially in cooperation with the intermediate member;
   a stent lock substantially disposed from a distal end to a proximal end thereof directly on the intermediate tubular member, wherein the stent lock is configured to releasably couple the stent-graft and the intermediate tubular member and is configured to be cylindrically shaped in an unconstrained configuration; and
   a tubular member lock configured to releasably couple the inner tubular member and the outer tubular member such that, when the inner tubular member and the outer tubular member are coupled, movement of the outer tubular member in an axial direction results in movement of the inner tubular member in the axial direction with respect to the intermediate tubular member so as to deploy the stent-graft.

2. The device of claim 1, wherein the outer tubular member defines a first length, the intermediate tubular member defines a second length, and the inner tubular member defines a third length, and wherein the first length is shorter than the second length and the second length is shorter than the third length.

3. The device of claim 1, wherein the inner tubular member defines an inner lumen configured to receive a guidewire therethrough.

4. The device of claim 1 further comprising a tip member attached to a distal end of the inner tubular member.

5. The device of claim 1, wherein the tubular member lock comprises a lock housing that is fixed to the outer tubular member, a pressing member that surrounds and is slideable along the inner tubular member, and a resilient sleeve that surrounds and is slideable along the inner tubular member.

6. The device of claim 1, wherein the stent lock is disposed at a distal end of the intermediate tubular member.

7. The device of claim 1, wherein the stent lock is disposed within a lumen of the stent-graft, and wherein the stent lock is configured to couple the stent-graft and the intermediate tubular member when a portion of the stent-graft overlying the intermediate tubular member is in a contracted state and to uncouple the stent-graft and the intermediate tubular member when the portion of the stent-graft is in an expanded state.

8. The device of claim 1, wherein the inner tubular member, the intermediate tubular member, and the outer tubular member are configured to move independently of each other.

9. The device of claim 1 further comprising a first handle attached to a proximal end of the inner tubular member and configured to move the inner tubular member.

10. The device of claim 1 further comprising a second handle attached to a proximal end of the outer tubular member and configured to move the outer tubular member.

11. The device of claim 10 further comprising a third handle attached to a proximal end of the intermediate tubular member, wherein movement of one of the second handle and the third handle towards the other of the second handle and the third handle serves to deploy the stent-graft from the outer tubular member.

12. The device of claim 11 further comprising a rigid tubular member attached to a proximal end of the second handle and configured to receive at least a portion of the intermediate tubular member and the inner tubular member therethrough.

13. The device of claim 12, wherein the rigid tubular member comprises a slot, and wherein the third handle is configured to engage the intermediate tubular member via the slot and to move axially along the slot.

14. The device of claim 13 further comprising a stop configured to be selectively fixed to the rigid tubular member via the slot at a location between the second handle and the third handle, wherein the stop serves to constrain the axial movement of the third handle along the rigid tubular member.

15. The device of claim 1, wherein the stent-graft comprises a self-expanding stent.

16. The device of claim 1, wherein the stent-graft comprises at least one layer of fabric.

17. The device of claim 16, wherein the at least one layer of fabric comprises braided metal strands.

18. The device of claim 16, wherein the at least one layer of fabric comprises metallic strands and polymeric strands.

19. A method for deploying a self-expanding stent-graft within a body lumen comprising:
  providing a device comprising:
    an outer tubular member defining an outer lumen;
    an intermediate tubular member at least partially disposed within the outer lumen,
  wherein the intermediate tubular member defines an intermediate lumen;
    an inner tubular member at least partially disposed within the intermediate lumen;
    a self-expanding stent-graft disposed in the outer lumen and at least partially overlying the intermediate member, wherein the stent-graft is configured to move axially with the intermediate member; and
    a stent lock substantially disposed from a distal end to a proximal end thereof directly on the intermediate tubular member, wherein the stent lock is configured to releasably couple the stent-graft and the intermediate tubular member and is configured to be cylindrically shaped in an unconstrained configuration;
  positioning the device within a body lumen;
  locking the inner tubular member to the outer tubular member; and
  retracting the outer tubular member and the inner tubular member with respect to the intermediate tubular member, thereby deploying the stent-graft.

20. The method of claim 19 further comprising advancing a distal end of the inner tubular member independently of the intermediate tubular member and the outer tubular member.

21. The method of claim 20 further comprising distally advancing the intermediate tubular member, wherein the steps of advancing a distal end of the inner tubular member, locking the inner and outer tubular members, and distally advancing the intermediate tubular member is done automatically.

22. The method of claim 20, wherein the device further comprises a first handle attached to a proximal end of the inner tubular member, wherein the step of advancing the distal end of the inner tubular member comprises moving the first handle distally.

23. The method of claim 19, wherein locking the inner tubular member to the outer tubular member comprises tightening a Tuohy Borst adapter.

24. The method of claim 19, wherein the device further comprises a second handle attached to a proximal end of the outer tubular member and a third handle attached to a proximal end of the intermediate tubular member, wherein the step of retracting the outer tubular member and the inner tubular member comprises moving the second handle towards the third handle.

25. The method of claim 24 further comprising constraining movement of the third handle with respect to the second handle.

26. The method of claim 19 further comprising recapturing the stent-graft within the outer lumen.

* * * * *